(12) United States Patent
Liljeström et al.

(10) Patent No.: US 6,566,093 B1
(45) Date of Patent: May 20, 2003

(54) ALPHAVIRUS CDNA VECTORS

(75) Inventors: Peter Liljeström, Sollentuna (SE); Henrik Garoff, Hägersten (SE)

(73) Assignee: Bioption AB, Sollentuna (SE)

( * ) Notice: Subject to any disclaimer, the term of this patent is extended or adjusted under 35 U.S.C. 154(b) by 0 days.

(21) Appl. No.: 09/061,912

(22) Filed: Apr. 17, 1998

Related U.S. Application Data (63) Continuation of application No. 08/704,567, filed as application No. PCT/SE95/00343 on Mar. 30, 1995, now abandoned.

(30) Foreign Application Priority Data

Mar. 30, 1995 (SE) ............................................. 9401091

(51) Int. Cl.[7] ..................... C12N 15/00; C12N 15/63; C12N 5/00
(52) U.S. Cl. .................. 435/69.1; 435/320.1; 435/325; 435/455; 424/199.1
(58) Field of Search ...................... 536/23.1; 435/320.1, 435/325, 455, 326, 475; 514/44; 424/199.1

(56) References Cited

U.S. PATENT DOCUMENTS 5,217,879 A 6/1993 Huang et al. ............... 435/69.1
5,814,482 A * 9/1998 Dubensky et al. .......... 435/69.3

FOREIGN PATENT DOCUMENTS

WO 9210578 6/1992
WO 9507994 3/1995

OTHER PUBLICATIONS

Crystal RG. Science 270:404–410.1995.*
Orkin SH and Motulsky AG. Report and Recommendations of the Panel to Assess the NIH investment in research on gene therapy, pp. 1–40, Dec. 7,1995.*
Verma IM and Somia N. Nature 389: 239–242. 1997.*
Schlessinger S. Trends in Biotechnology 11:18–22, 1993.*
Elroy–Stein O et al. Proc. Natl. Acad. Sci. USA 86:6126–6130. 1989.*
Xiong et al., Science, 243, pp 1188–1181 (1989).
Liljestrom et al., Bio/Technology, 9, 1356–1361 (1991).
Miller et al., FASEB, 9, 190–199 (1995).
Dubuisson et al., J. of Virology, 67(6):3363–3374 (1993).
Perrotta et al., Nature, 350:434–436 (1991).
Ledley, Hum. Gene. Ther., 2:77–83 (1991).
Hodgson, Exp. Opin. Ther. Patents, 5(5):459–468 (1995).
Culver et al., T.I.G., 10(5):174–178 (1994).
Marshall, Science, 269:1050–1055 (1995).
Bredenbeek et al., Journal of Virology 67(11):6439–6446, 1994.
Belinsky et al., Nucleic Acid Research 19(3):559–564, 1991.

* cited by examiner

*Primary Examiner*—Ram R. Shukla
(74) *Attorney, Agent, or Firm*—Birch, Stewart, Kolasch & Birch, LLP (57) ABSTRACT

The present invention is related to polynucleotide molecules and to their use for production of desired products after introduction into human or animal cells. In addition, the present invention is concerned with pharmaceutical compositions comprising said polynucleotide molecules and their use in prophylactic or therapeutic treatment methods. The present invention is also related to use of such polynucleotide molecules in animals to achieve expression of desired products, which can be recovered from the animal but do not give rise to any beneficial, e.g. therapeutic, activity in the animal. More specifically, the present invention is directed to alphaviruus cDNA vectors comprised of recombinant cDNA consisting of cDNA derived from an alphavirus and heterologous, i.e. foreign, cDNA encoding a desired substance.

27 Claims, 6 Drawing Sheets

ALPHAVIRUS CDNA VECTORS

This is a continuation of application Ser. No. 08/704,567, filed Sep. 10, 1996 (now abandoned) which is a 371 of PCT/SE95/00343, filed Mar. 30, 1995.

BACKGROUND OF THE INVENTION

The present invention is related to polynucleotide molecules and to their use for production of desired products after introduction into human or animal cells. In addition, the present invention is concerned with pharmaceutical compositions comprising said polynucleotide molecules and their use in prophylactic or therapeutic treatment methods. The present invention is also related to use of such polynucleotide molecules in animals to achieve expression of desired products, which can be recovered from the animal but do not give rise to any beneficial, e.g. therapeutical, activity in the said animal.

1. Field of the Invention

More specifically, the present invention is directed to alphavirus cDNA vectors comprised of recombinant cDNA consisting of cDNA derived from an alphavirus and heterologous, i.e. foreign, cDNA coding for a desired substance.

2. Description of Related Art

Alphavirus is a genus belonging to the family Togaviridae having single stranded RNA genomes of positive polarity enclosed in a nucleocapsid surrounded by an envelope containing viral spike proteins.

The Alphavirus genus comprises among others the Sindbis virus, the Semliki Forest virus (SFV), the Ross River virus and Venezuelan, Western and Eastern equine encephalitis viruses, which are all closely related. In particular, the Sindbis and the Semliki Forest viruses have been widely studied and the life cycle, mode of replication, etc, of these viruses are well known and thus, need not to be specifically discussed herein.

Alphaviruses replicate very efficiently in animal cells which makes them valuable as vectors for production of protein and nucleic acids in such cells.

Expression systems based on the Sindbis virus are disclosed in U.S. Pat. Nos. 5,091,309 an 5,217,879. The Sindbis virus vectors of U.S. Pat. No. 5,091,309 comprise RNA derived from Sindbis defective interfering (DI) RNA having heterologous RNA inserted therein.

In U.S. Pat. No. 5,217,879 self-replicating and self-packaging recombinant Sindbis virus RNA molecules are disclosed comprising a heterologous coding sequence and at least one Sindbis virus junction region able to direct Sindbis virus subgenomic messenger RNA synthesis in a host cell. RNA transcripts are synthesized in vitro by transcription of Sindbis virus cDNA which has been inserted in a plasmid under control of a promoter, such as SP6. The SP6 promoter and other promoters disclosed in connection with cDNA transcription are not functional in animal or human cells.

In WO 92/10578 (Garoff and Liljeström) an expression system based on alphaviruses is disclosed. An illustrative example of such viruses is the Semliki Forest virus (SFV). Earlier it was reported that a full-sized cDNA copy of the SFV RNA genome was contructed (Journal of Virology, Volume 65, pages 4107–4113, 1991). This was engineered into an SP6 transcription vector from which full-sized SFV genomic RNA molecules can be transcribed in vitro. The RNA can be transfected into animal cells, in which cells the RNA molecules will support normal wild-type virus infection, since the RNA molecules are of positive polarity and can function as messenger RNA molecules in the cells. Upon transfection, the first portion of the genome is translated into a polyprotein which self-cleaves into four non-structural proteins (nsP1–nsP4). These proteins constitute the alphavirus replicase and are responsible for the production of new full-length genomic RNA molecules as well as of a subgenomic RNA species starting from an internal promoter (26S promoter). They are also responsible for the capping of the 5' end of the new RNA molecules. The pSFV4 cDNA plasmid was further engineered into a general DNA expression plasmid by deleting portions of the coding region for the structural proteins and replacing such deleted portions with a linker region for insertion of foreign coding sequences (Bio/Technology, Volume 9, pages 1356–1361, 1991; Bio/Technology, Volume 11, pages 916–920, 1993). When foreign DNA coding sequences are inserted into these vectors, high amounts of foreign protein are obtained when virus structural proteins are translated from the RNA subgenome made by the alphavirus replicase.

According to WO 92/10578, an RNA molecule is provided, which is derived from an alphavirus RNA genome and is capable of efficient infection of animal cells, which RNA molecule comprises the complete alphavirus genome regions, which are essential for replication of the said alpha-virus RNA, and further comprises an exogenous RNA sequence capable of expressing its function in said host cell, said exogenous RNA sequence being inserted into a region of the RNA molecule which is non-essential to replication thereof. According to WO 92/10578 such RNA molecules can be transferred into animal cells by any means of transfection or by packaging of said RNA molecules into infectious alphavirus particles for later infection of animal cells. In both cases the transfected or infected RNA molecule will be able to replicate within the target animal cell and to express the exogenus RNA sequences inserted into said RNA molecule. Such molecules and strategies for their expression within the cell can be used as vaccines or strategies to vaccinate in order to prevent or treat infection or cancer.

Since it is difficult to engineer RNA molecules by current genetic engineering technology, manipulations of the Alphavirus genome, such as insertion of heterologous coding sequences, have been conducted on the corresponding cDNA molecule. Subsequently, the engineered cDNA molecule has been transcribed in vitro and the RNA transcripts obtained have been used to transform cells. These constructs comprising the engineered cDNA molecule cannot be transcribed in animal or human cells since the promoters used for transcriptional control is not functional in such cells.

Obviously, it would be to advantage if the cDNA molecule could be used per se to transform cells and achieve expression of a desired substance in these cells.

WO 90/11092 describes the use of naked polynucleotides as a pharmaceutical which operatively codes for a biologically active peptide. Such molecules are proposed to be injected into tissue for the in vivo expression of said peptide. Specifically, it is claimed that the polynucleotide is DNA and that the peptide may function as an antigen, and may thus be used as a vaccine (see also Science, Volume 259, pages 1745–1749; DNA and Cell Biology, Volume 12, number 9, entire volume, 1993). However, recombinant viral cDNA constructs comprising heterologous coding sequences which can be expressed in animal and human cells are not disclosed, therein, nor is a cDNA construct disclosed, which is transcribed into self-replicating RNA encoding the replicase necessary for its replication. Even though, use of DNA coding for a polypeptide and for a polymerase for transcribing the DNA is disclosed in WO 90/11092, the initial quantity of polymerase is provided by including mRNA coding therefore in the preparation, which mRNA is translated by the cell.

SUMMARY OF THE INVENTION

Thus, it is an object of the present invention to provide a recombinant cDNA molecule complementary to an alphavirus RNA and comprising an exogenous cDNA sequence, which molecule can be introduced into animal or human cells to achieve transcription or expression of said cDNA, desired products such as polynucleotides or proteins being produced in cells harbouring the cDNA-molecule.

In accordance with the present invention, this object is achieved by placing the complete cDNA molecule under transcriptional control of a promoter sequence functional in an animal or human cell. Said promoter sequence will initiate transcription by the DNA-dependent RNA polymerase encoded by the host cell, i.e. the animal or human cell harbouring the said cDNA molecule.

Accordingly, the present invention is concerned with a cDNA molecule complementary to at least part of an alphavirus RNA genome, which CDNA molecule comprises the complement of the complete alphavirus RNA genome regions, which are essential for replication of the said alphavirus RNA, and further comprises an exogenous cDNA sequence capable of expressing its function in an animal or human host cell, said exogenous cDNA sequence being inserted into a region of the cDNA molecule, which is non-essential to replication thereof, and said cDNA molecule being placed under transcriptional control of a promoter sequence functional in said animal or human cell.

The promoter sequence of the present invention may comprise a promoter of eukaryotic or prokaryotic origin. The promoter region may also include control elements for repression or enhancement of transcription. Suitable promoters are the cytomegalovirus immediate early promoter (pCMV) and the Rous sarcoma virus long-terminal repeat promoter (PRSV), since, in the case of these and similar promoters, transcription is performed by the DNA-dependent RNA polymerase of the host cell. Also the SP6, T3 or T7 promoters can be used provided that the cell has beforehand been transformed with genes encoding SP6, T3 or T7 RNA polymerase molecules which are either inserted into the chromosome or remain episomal. Expression of these (SP6, T3, T7) RNA polymerase-encoding genes is dependent on the host cell DNA-dependent RNA polymerase.

According to the present invention, the exogenous cDNA insert comprises the coding sequence for a desired product, suitable a biologically active protein or polypeptide, e.g. an immunogenic or antigenic protein or polypeptide, or a therapeutically active protein or polypeptide.

In accordance with another aspect of the invention, the exogenous cDNA insert comprises a sequence complementary to an RNA sequence, such as an anti-sense RNA sequence, which antisense sequence can be administered to an individual to inhibit translation of a complementary polynucleotide in cells of the said individual. The exogenous cDNA may also comprise additional sequences, such as a sequence complementary to an RNA sequence which is a self-cleaving ribozyme sequence. Suitably, the cDNA insert of the present invention is comprised of an integral sequence but the occurrence of interrupting viral sequence(s) is not precluded.

As per definition, in vitro means a process performed outside a living organism as opposed to in vivo which means that a process is performed inside a living organism. According to the present invention, a living organism is intended also to include living cells, such as cultured eukaryotic or prokaryotic cells.

In accordance with the present invention "transformation" is intended to mean introduction in general of exogenous polynucleotides sequences into the interior of a cell, eukaryotic or prokaryotic, and the exogenous polynucleotide sequence may remain extrachromosomal (episomal) or may be stably integrated into the cell genome. The mode of transformation is not crucial, but any means, known at present or that may be developed in the future, can be used according to the invention.

The present alphavirus cDNA vector is based on cDNA, which is complementary to an alphavirus RNA sequence. Once transcribed from the cDNA under transcriptional control of the heterologous promoter, the alphavirus RNA will be able to self-replicate by means of its own replicase and thereby amplifying the copy number of the transcribed recombinant RNA molecules. The replicase will also cap the 5' ends of each of these molecules. As a result of these events, high levels of expression of the heterologous insert cDNA sequences can be obtained in vivo in the animal or human individual Contrary to WO 92/10578, the present invention is directed to a cDNA construct, which can be introduced and transcribed per se in animal or human cells, rather than to RNA constructs. However, once the cDNA has been transcribed into RNA subsequent replicative steps and gene expression are in principle the same as described for vectors in WO 92/10578. The disclosure of WO 92/10578 is included in this application by reference thereto.

In the following, a suitable embodiment of the present invention is disclosed to illustrate the present invention without restriction thereof. According to this embodiment, a cDNA molecule comprising nucleotides 1 through 8265 of pSFV1 (WO 92/10578 and Bio/Technology, Volume 9, pages 1356–1361, 1991), containing a heterologous insert e.g. encoding a viral antigen (such as the influenza hemagglutinin protein, influenza nucleoprotein, HIV-1 envelope protein, HIV-1 gag-pol, HIV-1 nef), or a therapeutic protein (such as human growth hormone, interleukin-2, erythropoietin, or factor VIII), or a ribozyme or anti-sense RNA, functionally inserted downstream of the alphavirus subgenomic promoter, is cloned under the CMV promoter in a plasmid in such a way, that the expression of the cDNA insert is driven by the CMV promoter. Downstream from the 3' end of the cDNA insert, a transcription termination signal (e.g. derived from SV40) is positioned to stop transcription. When this plasmid is transferred into an animal cell, the CMV promoter will guide the transcription of the cDNA insert with its heterologous insert to form one long RNA molecule. This will be transported to the cytoplasm where it is used as mRNA for translation of the nonstructural replicase proteins of the SFV vector. Since the initially transcribed RNA molecule carries sequences required for its replication, the replicase proteins will subsequently initiate replication of the RNA molecule to minus strand intermediates. Subsequently, the SFV replicase will use the internal 26S promoter on the minus strand of the recombinant RNA molecule to produce the messenger RNA molecule encoding the heterologous protein or giving rise to RNA. The RNA replicative events have been described in more detail in WO 92/10578.

Efficient replication of the alphavirus genome is known to require proper 5' and 3' ends.

Thus, according to a suitable embodiment of the invention a self-cleaving ribozyme sequence is inserted within the end region of the cDNA insert. This ribozyme molecule is positioned at the 3' end of the alphavirus genomic sequence in such a way that it, when cleaved, will generate the proper alphavirus 3' end. Accordingly, when the primary transcript has been made and elongation terminated at the transciption stop signal (e.g. SV40), the ribozyme sequence, carried within the 3' end domain of the transcipt will self-cleave to generate the proper 3' end.

In accordance with another embodiment of the present invention an exact 3' end of the alphavirus RNA molecule is achieved with use of linearized cDNA molecules for the initial transfection. Thus, synthesis from the promoter will result in run-off transcription giving molecules with proper 3' ends.

In accordance with a suitable embodiment of the invention, in the recombinant cDNA the alphavirus derived cDNA molecule regions comprise sequences complementary to a 5' terminal portion, the coding region(s) for non-structural proteins required for RNA replication, the subgenome promoter region and a 3' terminal portion of said viral RNA.

Another embodiment of the invention is concerned with a recombinant cDNA, wherein the exogenous cDNA sequence encodes a foreign polypeptide or gives rise to RNA, said sequence being integrated into the cDNA complementary to the alphavirus subgenomic RNA substituting one or more nucleotides thereof.

A further embodiment of the invention is related to a recombinant cDNA, wherein the exogenous cDNA sequence encodes a foreign polypeptide or gives rise to RNA, said sequence being integrated into the alphavirus subgenomic RNA without substituting any nucleotides thereof.

A broad range of host cells of animal (including human) origin can be used according to the present invention. Such host cells can be selected from avian, mammalian, amphibian, insect and fish cells. Illustrative of mammalian cells are human, monkey, hamster, mouse and porcine cells. Suitable avian cells are chicken cells.

The present cDNA molecules can be used for the treatment of infectious disease, cancer or metabolic disorder or other types of deficiencies in animals and humans. They can also be used for prophylactic treatment or vaccination of animals or humans to prevent infectious disease or cancer. The molecules constitute themselves pharmaceuticals, which operatively code for a biologically active polypeptide or give rise to biologically active polynucleotides, such as antisense RNA, and can be administered directly as such or in combination with other compounds into the animal or human for the expression of the desired sequences.

According to one aspect of the invention, said molecules are used as naked plasmid cDNA molecules and can be administered by intramuscular, intradermal, intranasal, epidermal, mucosal, intravenous route or any other route.

In accordance with another aspect of the invention, the present molecules are mixed with lipids or other compounds to enhance delivery (Trends in Biotechnology, Volume 11, pages 211–215, 1993). The cDNA can also be linked to other carrier molecules which bind to cellular receptors for uptake into cells (Trends in Biotechnology, Volume 11, pages 202–205, 1993). Such combined strategies can be used by any route of administration. The naked cDNA can also be administered by the means of particle bombardment (Current Opinion in Biotechnology, Volume 4, pages 583–590, 1993).

Moreover, the present cDNA polynucleotide can be administered as part of the genome of another virus, such as a retrovirus. It has been shown earlier that the alphavirus replicase, when produced from a heterologous viral promoter can efficiently perform replication of alphavirus RNA molecules (Journal of Virology, Volume 65, pages 6714–6723, 1991; Virus Research, Volume 23, pages 209–222, 1992).

The present invention is also related to a method, wherein the present cDNA, or the cultured cells comprising this cDNA, is (are) introduced into an animal to produce a product by expression of said cDNA, which product can be recovered from the animal and which product has no effect, which is beneficial to the individual animal, wherein it is produced. Suitably, the expression product is secreted into a body fluid, such as blood, milk or ascites, and is recovered by collection of said fluid. In accordance with one embodiment of this method, the expression product has therapeutic or prophylactic activity and is recovered in a body fluid, such as milk.

In another embodiment of this method, expression of a cDNA, comprising exogenous cDNA coding for an immunogenic or antigenic protein or polypeptide, is achieved and elicits an antibody response, antibodies being collected from the animal in a body fluid, such as whole blood, serum or ascites.

According to a further embodiment of this method, the cDNA comprises exogenous cDNA coding for an antigenic determinant, antigens or immunogens being produced by expression of the cDNA and recovered from the animal in a body fluid, such as whole blood or serum.

DESCRIPTION OF THE DRAWINGS

FIG. 1(A) and FIG. 1(B): A DNA/RNA layered system. A DNA vector according to one embodiment of the present invention is illustrated where the SFV cDNA encoding the SFV replicase proteins (REPLICASE GENES) is cloned under the CMV promoter (pCMV). The exogenous genes (EXOGENOUS SEQUENCE) are inserted after the replicase region, under the subgenomic promoter of SFV. The 5' and 3' sequences required for replication of the SFV RNA are indicated by black boxes. The SFV derived sequences end by the poly-A sequence (A). The self-cleaving ribozyme sequence (R) is situated immediately after the poly-A sequence. Sequences required for termination of transcription (from pCMV) and polyadenylation of the transcript are placed last in the construct (TRANSCRIPTION TERMINATION). The first event is the transcription, from pCMV, of the full-length construct. This leads to the production of a RNA molecule which is of positive polarity with respect to the replicase genes, i.e. the RNA can function as a mRNA for the translation of the replicase proteins (1). Immediately after transcription, the ribozyme cleaves itself off the chain (2). The resulting RNA molecule is transported to the cytoplasm of the cell (3). In the cytoplasm, the first part of the RNA is translated to produce the SFV replicase (REP). This replicase will then copy the complete RNA to minus-strand intermediates (4). The minus-strand intermediates will then serve as templates for production, by the SFV replicase, of new full-length positive strand RNA molecules (5), which subsequently can be used for new rounds of minus-strand synthesis thus amplifying the overall production of the desired product (7). The minus-strand intermediates also serve as templates for production of another species of RNA, initiation of synthesis occurring at the SFV subgenomic promoter (right-ward arrow) (6). This exogenous RNA either encodes the desired exogenous protein, or alternatively, may itself constitute the desired end-product (such as a ribozyme or an anti-sense molecule) (8).

FIG. 2: Alphavirus cDNA polynucleotide under the transcriptional control of a heterologous promoter. A, a heterologous promoter such as pCMv, pRSV, SP6; B, 5' end of alphavirus genomic RNA including sequences required for replication of said RNA; C, genomic region of alphavirus nonstructural region encoding the replicase proteins nsP1, nsP2, nsP3 and nsP4; D, subgenomic promoter (26S) of an alphavirus; E, heterologous cDNA sequence functionally coding (in the context of the subgenomic replicon of the alphavirus) for a heterologous protein or RNA; F, 3' end sequences required for replication of the recombinant RNA; G, Poly-A sequence (may be optional); H, eukaryotic transcription stop signal such as one derived from SV40.

FIG. 5: Self-cleaving activity of hepatitis delta ribozyme in the context of the SFV RNA. (A) Plasmid pSFV-H1-Delta with the ribozyme sequence inserted at position 5284. (B) Gel analysis of the in vitro cleavage products of RNA complementary to pSFV-H1-Delta. Note that the uncleaved form and the 5' cleaved form of the primary transcript are so large (5502 and 5284 respectively), that they are not resolved on the gel and hardly migrate into the gel.

DETAILED DESCRIPTION OF THE INVENTION

EXAMPLE 1

Figure 4:
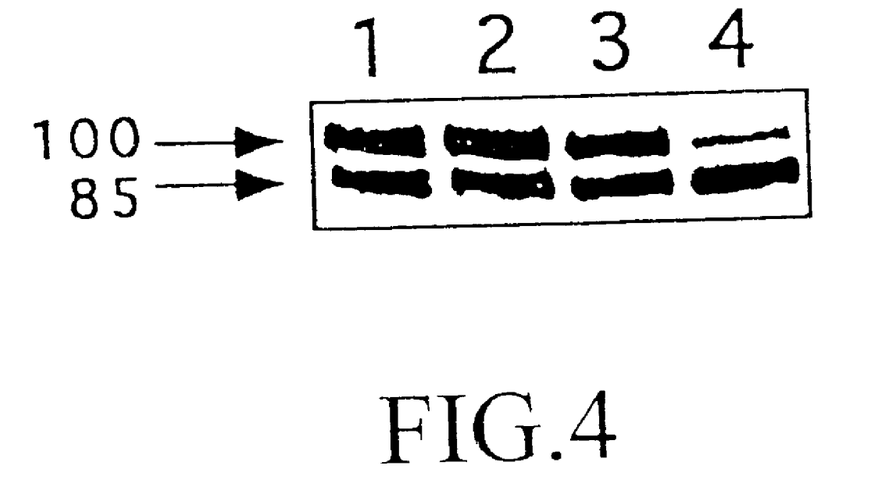
FIG. 4: Self-cleaving activity in vitro of the hepatitis delta ribozyme. Plasmid pSA1 was used as template for in vitro transcription of RNA. The RNA products were analyzed by polyacrylamide gel electrophoresis and autoradiography.

Self-cleaving Activity In vitro of the Hepatitis Delta Ribozyme pSA1 (Nature, vol 350, pages 434–436, 1991) was linearized with BamHI before transcription. In vitro transcription was performed as described earlier (Journal of Virology, vol 65, pages 4107–4113, 1991, Current Protocols in Molecular Biology, Unit. 16.20, 1994, Greene & Wiley Interscience) in the presence of $^{35}$S-rCTP to label the RNA synthesized. After 60 min transcription, one fourth of the sample was frozen at −80° C. The rest was divided into three parts, of which the first was incubated at 56° C. for 30 min in the presence of 25 mM EDTA. The second was incubated at 37° C. for 30 min without EDTA, and the third at 56° C. for 30 min without EDTA. After incubation, all samples were analyzed on an 8% polyacrylamide sequencing gel with Tris-borate buffer containing urea (Current Protocols in Molecular Biology, Greene & Wiley Interscience). The result was visualized by autoradiography. As shown in FIG. 4, after 60 min of transcription, about 50% of the full-length RNA synthesized (100 nucleotides) has already been cleaved to a shorter product (85 nucleotides) (lane 1). Elevated temperatures are known to enhance self-cleaving activity, whereas EDTA is inhibiting the same, since the reaction is dependent on magnesium ions (Nature, vol 350, pages 434–436, 1991). Lane 2 shows that no additional cleavage occurred even at 56° C. when magnesium was chelated from the reaction by EDTA. In contrast, further incubation of the RNA at 37° C. (lane 3) or at 56° C. (lane 4) in the absence of chelating agent showed that self-cleaving activity was present and that the full-length RNA progressively was shortened to its 85 nucleotide product.

EXAMPLE 2

Figure 5A:
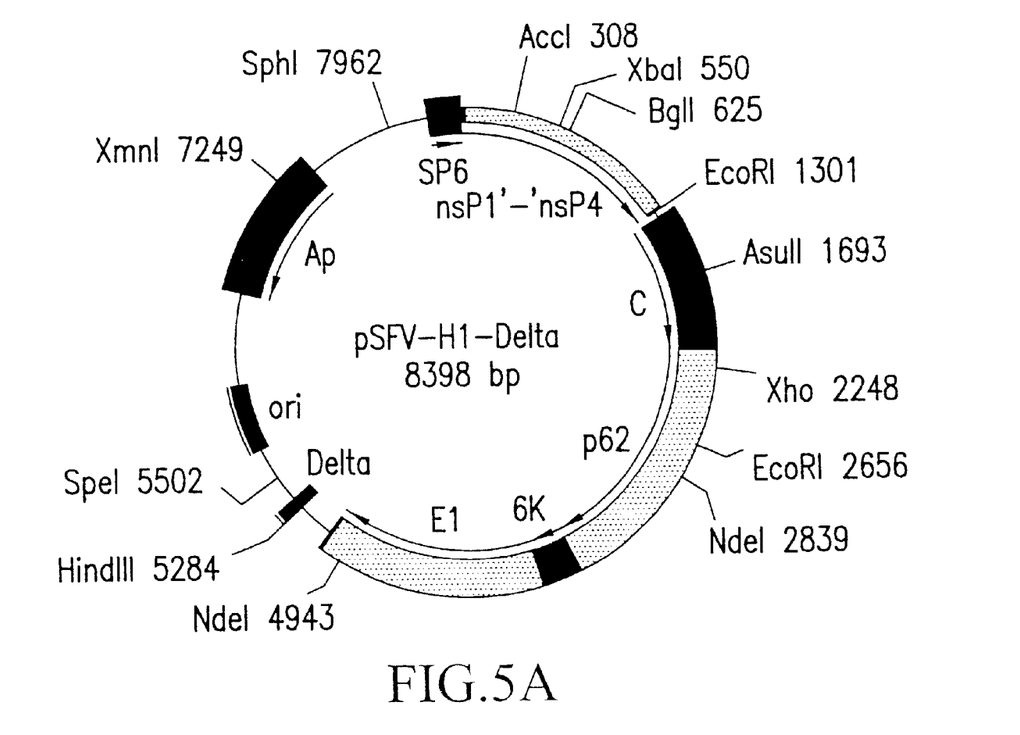
Figure 5B:
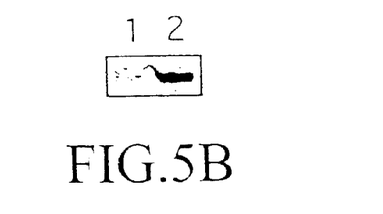

Self-cleaving Activity In vitro of Hepatitis Delta Ribozyme in the Context of the SFV RNA To test whether the ribozyme sequence can function in the context of a SFV RNA molecule, a DNA fragment corresponding to the hepatitis delta ribozyme sequence from pSA1 was synthesized and cloned into the HindIII restriction endonuclease cleavage site 5284 of Helper 1 (Bio/Technology, vol 9, pages 1356–1361, 1991) to generate plasmid pSFV-H1-Delta (FIG. 5A). The cloning was performed using standard techniques (Current Protocols in Molecular Biology, Greene & Wiley Interscience). The plasmid was then linearized with SpeI and in vitro transcription performed as described in EXAMPLE 1. Half of the sample was frozen for control whereas the other half was further incubated at 56° C. for an additonal 60 min. The samples were then analyzed by gel electrophoresis and autoradiography as described in EXAMPLE 1. The result is shown in FIG. 5B. Lane 1 represents the small cleavage product (167 nucleotides) generated during self-cleavage during transcription. When the transcripts have been incubated for an additional 60 min at 56° C. (lane 2), a marked increase in the 167 nucleotide species is observed, indicating that self-cleavage is progressing efficiently.

EXAMPLE 3

Self-cleavage of Hepatitis Delta Ribozyme In vivo in the Context of an SFV RNA

Plasmids pSFV3-lacZ (Bio/Technology, vol 9, pages 1356–1361, 1991), pSFV-Helper 1 (Bio/Technology, vol 9, pages 1356–1361, 1991), and pSFV-H1-Delta were linearized with SpeI and RNA synthesized in vitro using SP6 RNA polymerase as described above. Immediately after transcription, EDTA was added to 25 mM and the RNAs put on ice. 20 μl of the lacZ RNA was mixed with 20 μl of Helper 1 RNA or with 20 or 40 μl of H1-Delta RNA (since self-cleavage occurs with up to 50% during transcription, the doubling of the amount of H1-Delta RBA was designed to compensate for the loss of full-length RNA due to this processing). The mixed RNAs were then used to transfect baby hamster kidney cells (BHK) as described earlier (Bio/Technology, vol 9, pages 1356–1361, 1991), to prepare a virus stock via in vivo packaging of lacZ RNA into SFV particles (Bio/Technology, vol 9, pages 1356–1361, 1991). The 24 h supernatant of these cultures were then used to infect monolayers of BHK cells and after 16 h the cells were stained with Xgal to visualize expression of beta-galactosidase (lacZ protein). Using different amounts of medium it was possible to determine the titre of the virus stock obtained from the in vivo packaging reaction. Only the Helper 1 RNA supported the production of an infectious stock, giving rise to a titre of $5 \times 10^7$ infectious particles per ml (a total of $5 \times 10^8$ particles from $10^7$ transfected cells). In contrast, neither of the experiments involving the H1-Delta RNA produced any detectable virus. This shows that the self-cleavage of the ribozyme sequence present in the H1-Delta RNA effectively removes the 3' sequences needed for RNA replication so that trans-complemention by the helper construct cannot take place.

EXAMPLE 4

Figure 1A:
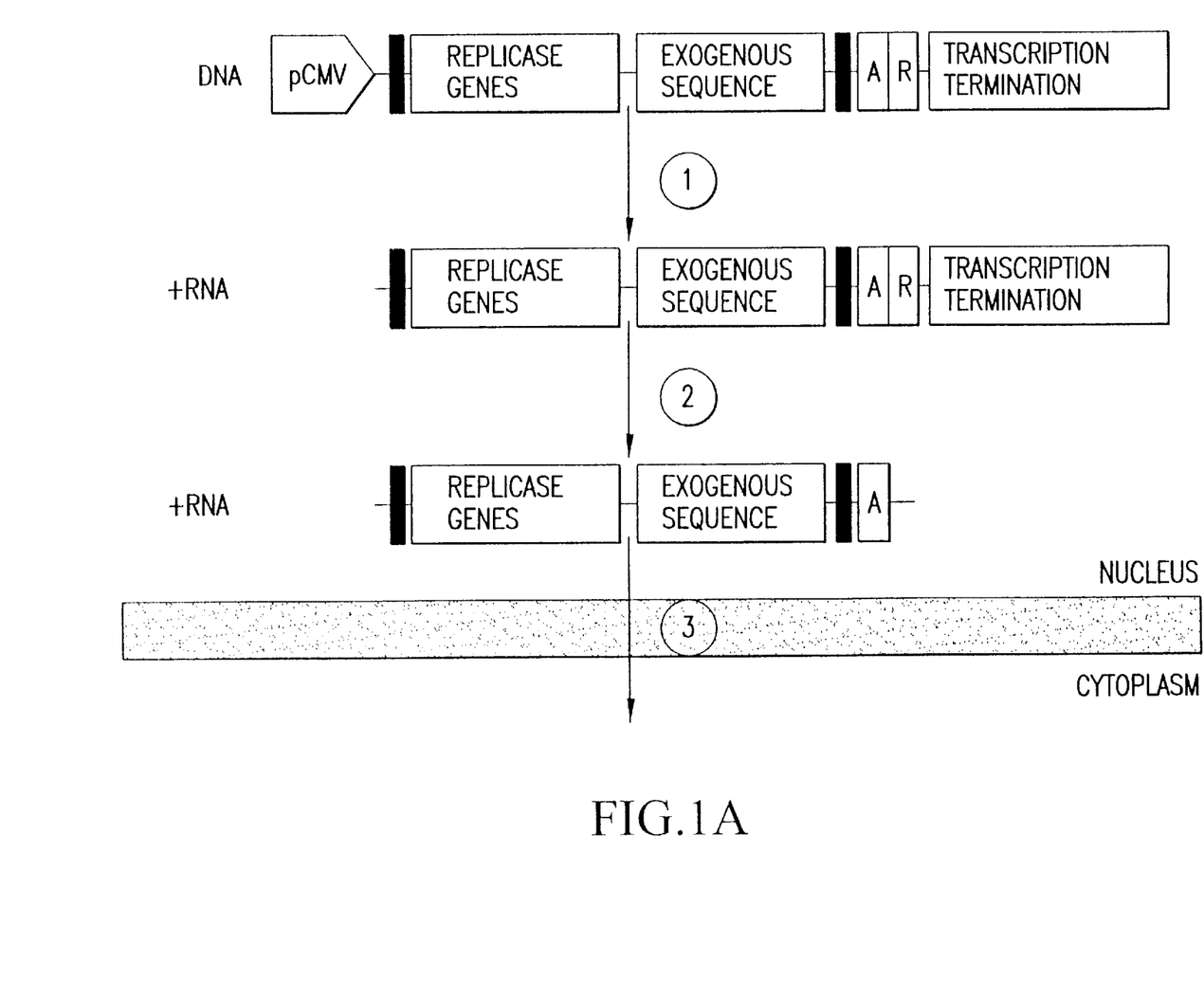
Figure 1B:
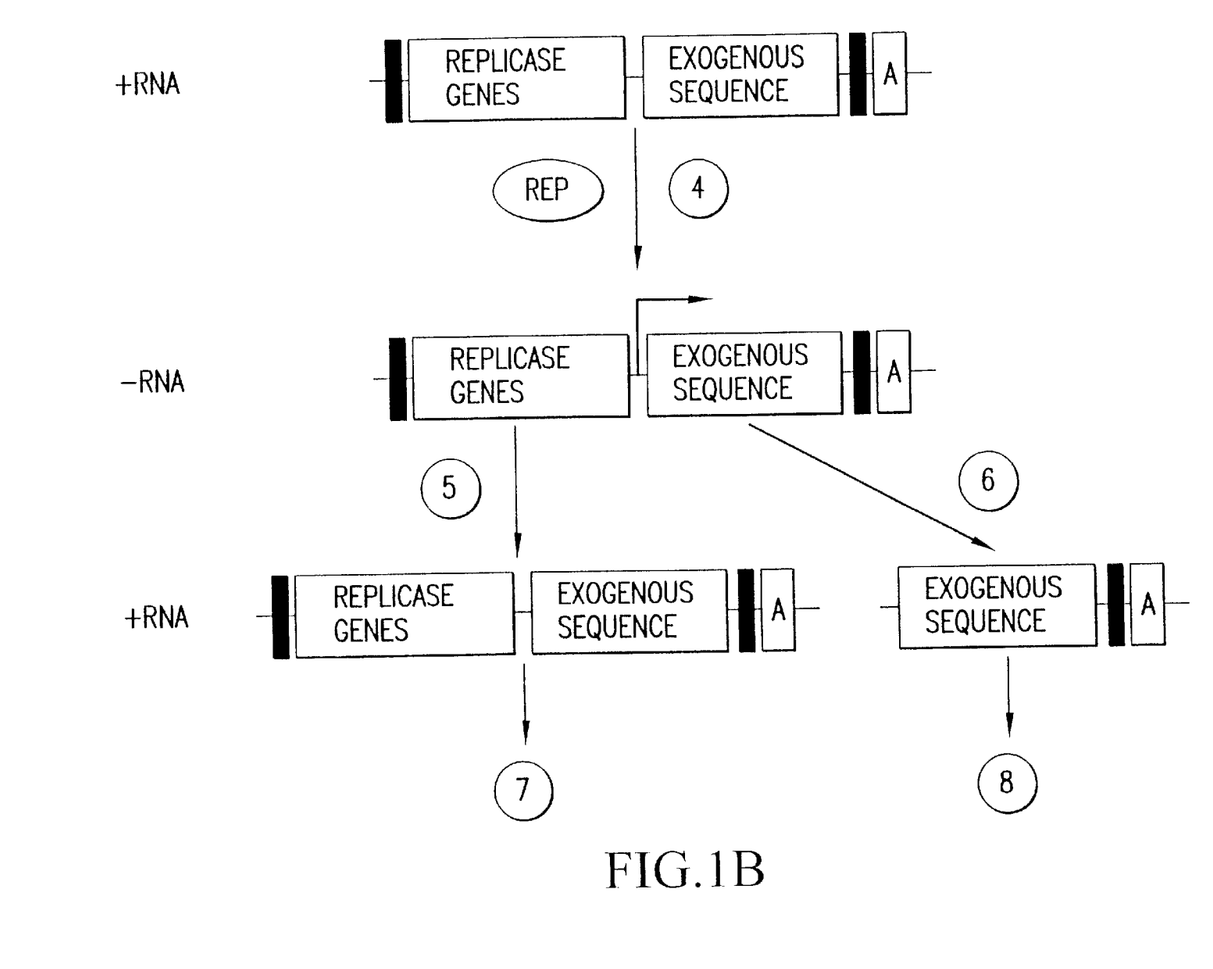
Figure 2:
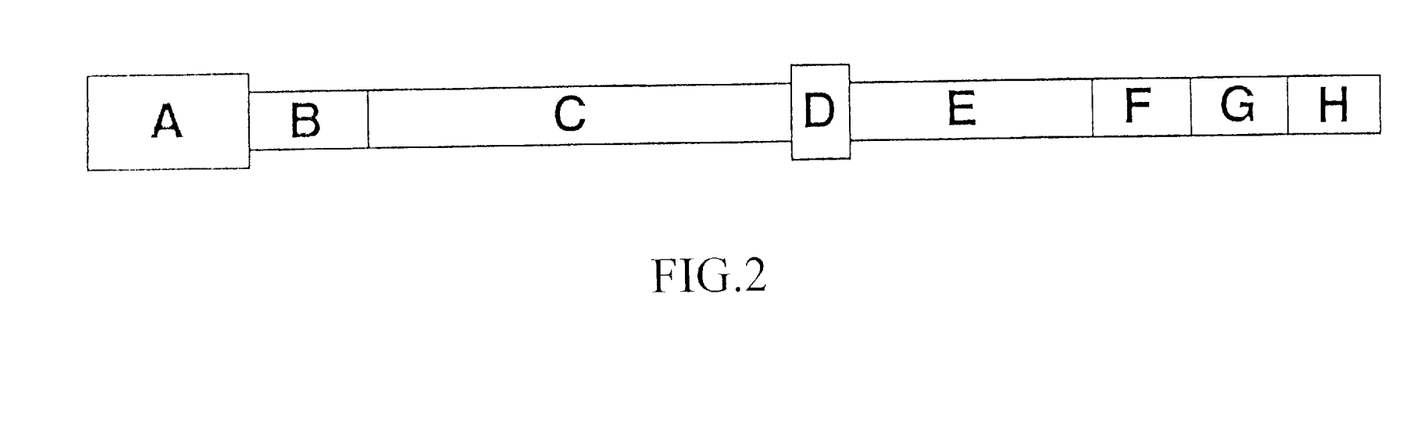
Figure 3:
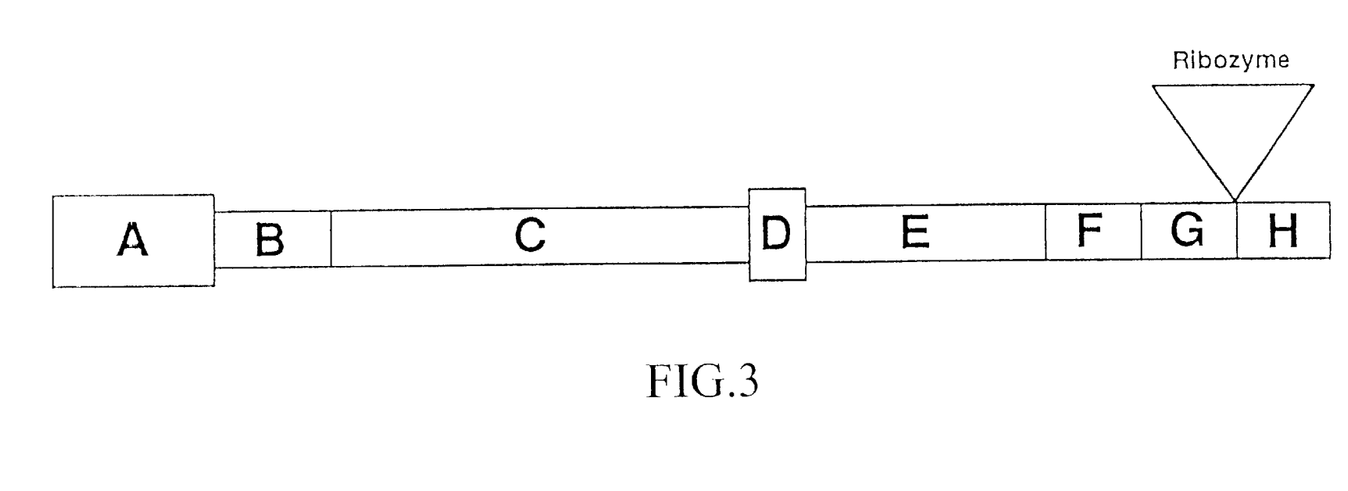
FIG. 3: Alphavirus cDNA polynucleotide under the transcriptional control of a heterologous promoter and including a self-cleaving ribozyme sequence. A, a heterologous promoter such as pCMV, pRSV, SP6; B, 5' end of alphavirus genomic RNA including sequences required for replication of said RNA; C, genomic region of alphavirus nonstructural region encoding the replicase proteins nsP1, nsP2, nsP3 and nsP4; D, subgenomic promoter (26S) of an alphavirus; E, heterologous cDNA sequence functionally encoding (in the context of the subgenomic replicon of the alphavirus) a heterologous protein or RNA; F, 3' end sequences required for replication of the recombinant RNA; G, poly-A sequence (may be optional); H, eukaryotic transcription stop signal such as one derived from SV40. The ribozyme sequence is presented to be inserted between the Poly-A stretch and the transcription stop signal in such a way, that it when self-cleaved will generate the authentic 3' end of a genomic alphavirus sequence.

Expression of LacZ from a DNA/RNA Layered Vector According to FIG. 3

A plasmid constructed as outlined in FIG. 3 using the CMV promoter and having as heterologous sequence (E) the gene encoding the beta-galactosidase protein of *Escherichia coli* was transfected into $10^6$ BHK-21 cells using Lipofectin (Life Technologies Inc. Gaithersburg, Md, USA). Transfection was done according to recommendations from the supplier. For a control vector, the same LacZ gene was cloned as a BamHI fragment into the multicloning site of the pBK-CMV plasmid (Stratagene Inc., La Jolla, Calif., USA). This plasmid expresses the beta-galactosidase gene directly from the CMV promoter. After 16 h incubation at 37° C., medium was removed and the cells were washed with PBS and fixed at −20° C. for 5 minutes with 100% methanol, followed by a new wash with PBS. Cells ware stained with Xgal (5-bromo-4-chlor-3-indolyl-beta-D-galactopyranoside) as described previously (EMBO Journal, vol 5, pages 3133–3142, 1986). After staining, the control experiment showed LacZ expression (Xgal positive) in cells with a frequency of about 0.03. In the experiment using the DNA/RNA layered construct, the frequency of transfection was 0.005. Accordingly, while the frequency of transfection in this particular experiment was rather low for the DNA/RNA layered vector, the expression of beta-galactosidase was high judging from the Xgal staining. Therefore, this experiment gives proof of principle and general feasibility of this technology.

What is claimed is:

1. A DNA construct comprising a first polynucleotide that comprises a promoter functional in a mammalian cell, operatively linked to a second polynucleotide that encodes the (+) strand of a recombinant alphavirus genome that comprises in the order stated:
   (a) the complement of the 5' terminal genomic sequence of an alphavirus that is essential for replication of the RNA of said alphavirus, (b) a nucleotide sequence encoding the replicase proteins of said alphavirus, (c) an alphavirus subgenomic promoter, (d) at least one nucleotide sequence exogenous to said alphavirus, operatively linked to said alphavirus subgenomic promoter to provide for transcription of said at least one nucleotide sequence exogenous to said alphavirus when said DNA construct is present in a host cell, (e) the complement of the 3' terminal genomic sequence of said alphavirus that is essential for replication of the RNA of said alphavirus, and (f) a nucleotide sequence complementary to a nucleotide sequence that functions as a self-cleaving ribozyme wherein said nucleotide sequence complementary to a nucleotide sequence that functions as a self-cleaving ribozyme is located at the 3'-end of said nucleotide sequence encoding the (+) strand of said alphavirus genome.

2. The DNA construct of claim 1, wherein the promoter effective in a mammalian cell is a cytomegalovirus immediate early promoter or a Rous sarcoma virus long terminal repeat promoter.

3. The DNA construct of claim 1, wherein said alphavirus is Semliki Forest Virus.

4. The DNA construct of claim 2, wherein said alphavirus is Semliki Forest Virus.

5. The DNA construct of claim 1, wherein at least one nucleotide sequence exogenous to said alphavirus encodes a biologically active or antigenic protein or polypeptide.

6. The DNA construct of claim 2, wherein at least one nucleotide sequence exogenous to said alphavirus encodes a biologically active or antigenic protein or polypeptide.

7. The DNA construct of claim 3, wherein at least one nucleotide sequence exogenous to said alphavirus encodes a biologically active or antigenic protein or polypeptide.

8. The DNA construct of claim 4, wherein at least one nucleotide sequence exogenous to said alphavirus encodes a biologically active or antigenic protein or polypeptide.

9. The DNA construct of claim 1, wherein at least one nucleotide sequence exogenous to said alphavirus encodes a polyribonucleotide that functions as an antisense RNA or ribozyme.

10. The DNA construct of claim 2, wherein at least one nucleotide sequence exogenous to said alphavirus encodes a polyribonucleotide that functions as an antisense RNA or ribozyme.

11. The DNA construct of claim 3, wherein at least one nucleotide sequence exogenous to said alphavirus encodes a polyribonucleotide that functions as an antisense RNA or ribozyme.

12. The DNA construct of claim 4, wherein at least one nucleotide sequence exogenous to said alphavirus encodes a polyribonucleotide that functions as an antisense RNA or ribozyme.

13. The DNA construct of claim 1, wherein said nucleotide sequence that encodes a self-cleaving ribozyme is derived from hepatitis delta virus.

14. The DNA construct of claim 2, wherein said nucleotide sequence that encodes a self-cleaving ribozyme is derived from hepatitis delta virus.

15. The DNA construct of claim 3, wherein said nucleotide sequence that encodes a self-cleaning ribozyme is derived from hepatitis delta virus.

16. The DNA construct of claim 4, wherein said nucleotide sequence that encodes a self-cleaving ribozyme is derived from hepatitis delta virus.

17. A host-vector system comprising (I) a vector comprising:
   (i) a first polynucleotide that comprises a bacteriophage promoter that is operatively linked to
   (ii) a second polynucleotide that encodes the (+) strand of a recombinant alphavirus genome that comprises in the order stated: (a) the complement of the 5' terminal genomic sequence of an alphavirus that is essential for replication of the RNA of said alphavirus, (b) a nucleotide sequence encoding the replicase proteins of said alphavirus, (c) an alphavirus subgenomic promoter, (d) at least one nucleotide sequence exogenous to said alphavirus, operatively linked to said alphavirus subgenomic promoter to provide for transcription of said at least one nucleotide sequence exogenous to said alphavirus when said DNA construct is present in a host cell, (e) the complement of the 3' terminal genomic sequence of said alphavirus that is essential for replication of the RNA of said alphavirus, and (f) a nucleotide sequence complementary to a nucleotide sequence that functions as a self-cleaving ribozyme wherein said nucleotide sequence complementary to a nucleotide sequence that functions as a self-cleaving ribozyme is located at the 3'-end of said nucleotide sequence encoding the (+) strand of said alphavirus genome; and (II) a mammalian host cell that expresses the corresponding bacteriophage RNA polymerase.

18. The host-vector system of claim 17, wherein said bacteriophage promoter is a SP6, T3 or T7 promoter and said bacteriophage RNA polymerase is the corresponding SP6, T3 or T7 polymerase.

19. The host-vector system of claim 17 or 18, wherein said at least one nucleotide sequence exogenous to said alphavirus is a nucleotide sequence that encodes a biologically active protein or biologically active polypeptide or an antigenic polypeptide or an antigenic protein or a polyribonucleotide that functions as an antisense RNA or a polyribonucleotide that functions as a ribozyme.

20. A method for producing a biologically active or antigenic protein or polypeptide comprising transforming a mammalian cell with the DNA construct of claim 5, 6, 7 or 8, culturing the transformed mammalian cell so produced under conditions appropriate for expression of said biologically active or antigenic polypeptide or protein, and isolating the biologically active or antigenic polypeptide or protein thus expressed.

21. A method for producing a biologically active or antigenic protein or polypeptide comprising culturing the transformed host cell of the host-vector system of claim 17 under conditions such that a biologically active or antigenic polypeptide or protein encoded by the nucleotide sequence exogenous to said alphavirus is expressed and isolating the biologically active or antigenic polypeptide or protein thus expressed.

22. A method for producing a biologically active or antigenic protein or polypeptide comprising culturing the transformed host cell of the host-vector system of claim 18 under conditions such that a biologically active or antigenic polypeptide or protein encoded by the nucleotide sequence exogenous to said alphavirus is expressed and isolating the biologically active or antigenic polypeptide or protein thus expressed.

23. A method for producing a biologically active or antigenic protein or polypeptide comprising culturing the transformed host cell of the host-vector system of claim 19 under conditions such that a biologically active or antigenic polypeptide or protein encoded by the nucleotide sequence exogenous to said alphavirus is expressed and isolating the biologically active or antigenic polypeptide or protein thus expressed.

24. A method for producing a biologically active or antigenic protein or polypeptide comprising culturing the transformed host cell of the host-vector system of claim 20 under conditions such that a biologically active or antigenic polypeptide or protein encoded by the nucleotide sequence exogenous to said alphavirus is expressed and isolating the biologically active or antigenic polypeptide or protein thus expressed.

25. A host cell transformed with the DNA construct of claim 1.

26. The DNA construct of claim 1, wherein said promoter is a bacteriophage promoter and said mammalian cell is a transgenic mammalian cell expressing the corresponding bacteriophage RNA polymerase.

27. A host cell transformed with the DNA construct of claim 26.

* * * * *

UNITED STATES PATENT AND TRADEMARK OFFICE
CERTIFICATE OF CORRECTION

PATENT NO. : 6,566,093 B1
DATED : May 20, 2003
INVENTOR(S) : Peter Liljeström and Henrik Garoff It is certified that error appears in the above-identified patent and that said Letters Patent is hereby corrected as shown below:

<u>Title page,</u>
Item [30], Foreign Application Priority Data, replace "Mar. 30, 1995" with -- Mar. 31, 1994 --

Signed and Sealed this

Thirty-first Day of August, 2004

JON W. DUDAS
*Director of the United States Patent and Trademark Office*